US009738943B2

United States Patent
Ekman et al.

(10) Patent No.: US 9,738,943 B2
(45) Date of Patent: Aug. 22, 2017

(54) PROCESS FOR CONTROLLED LIQUEFACTION OF A BIOMASS FEEDSTOCK BY TREATMENT IN HOT COMPRESSED WATER

(75) Inventors: Rune Ekman, Skanor (SE); Andreas Gram, Höör (SE); Haukur Johannesson, Lund (SE)

(73) Assignee: RENMATIX, INC., King of Prussia, PA (US)

( * ) Notice: Subject to any disclaimer, the term of this patent is extended or adjusted under 35 U.S.C. 154(b) by 1052 days.

(21) Appl. No.: 13/882,868

(22) PCT Filed: Oct. 28, 2011
(Under 37 CFR 1.47)

(86) PCT No.: PCT/SE2011/051292
§ 371 (c)(1),
(2), (4) Date: Oct. 6, 2015

(87) PCT Pub. No.: WO2012/060767
PCT Pub. Date: May 10, 2012

(65) Prior Publication Data
US 2016/0053337 A1     Feb. 25, 2016

Related U.S. Application Data

(60) Provisional application No. 61/409,269, filed on Nov. 2, 2010.

(30) Foreign Application Priority Data

Nov. 1, 2010    (SE) ........................................ 1051145

(51) Int. Cl.
*C13K 1/02*      (2006.01)
*B01J 3/00*       (2006.01)
(Continued)

(52) U.S. Cl.
CPC ................. *C13K 1/02* (2013.01); *B01J 3/008* (2013.01); *C08B 1/003* (2013.01); *C08H 8/00* (2013.01);
(Continued)

(58) Field of Classification Search
CPC ........................................................ C13K 1/02
See application file for complete search history.

(56) References Cited

U.S. PATENT DOCUMENTS 3,413,189 A    11/1968   Backlund
3,766,077 A    10/1973   Hwa et al.
(Continued)

FOREIGN PATENT DOCUMENTS

BR    11 2013 010659 0     10/2011
CA         2660990 A1       8/2009
(Continued)

OTHER PUBLICATIONS

Matsunaga et al, Super-Rapid Chemical Conversion of Sugi Wood by Supercritical and Subcritical Water Treatment, 2001, vol. 50, issue 5, pp. 325-332.*
(Continued)

*Primary Examiner* — Melvin C Mayes
*Assistant Examiner* — Stefanie Cohen
(74) *Attorney, Agent, or Firm* — Ballard Spahr LLP

(57) ABSTRACT

The present invention describes a process for a controlled conversion of a biomass feedstock, wherein the process comprises the steps of:
    loading the biomass feedstock to at least one reactor;
    liquefaction of the biomass feedstock into a monomer and/or oligomer sugar mixture in said reactor by treatment in hot compressed liquid water (HCW) at sub- and/or super-critical condition; and
(Continued)

Flow experiment removal of the monomer and/or oligomer sugar mixture, being the product molecules, to avoid continued detrimental decomposition.

20 Claims, 2 Drawing Sheets

(51) Int. Cl.
| | |
|---|---|
| *C13K 13/00* | (2006.01) |
| *C08B 1/00* | (2006.01) |
| *C08H 8/00* | (2010.01) |
| *C12P 7/10* | (2006.01) |
| *C13K 11/00* | (2006.01) |
| *D21B 1/02* | (2006.01) |

(52) U.S. Cl.
CPC ............... *C12P 7/10* (2013.01); *C13K 11/00* (2013.01); *C13K 13/00* (2013.01); *C13K 13/007* (2013.01); *D21B 1/021* (2013.01); *B01J 2219/00029* (2013.01); *B01J 2219/00036* (2013.01); *B01J 2219/00177* (2013.01); *C12P 2201/00* (2013.01); *Y02E 50/16* (2013.01); *Y02P 20/544* (2015.11)

(56) References Cited

U.S. PATENT DOCUMENTS

| | | | |
|---|---|---|---|
| 3,985,659 | A | 10/1976 | Felicetta et al. |
| 4,175,066 | A | 11/1979 | Shibazaki et al. |
| 4,196,094 | A | 4/1980 | Johnson et al. |
| 4,342,831 | A | 8/1982 | Faber et al. |
| 4,461,648 | A | 7/1984 | Foody |
| 5,041,192 | A | 8/1991 | Sunol et al. |
| 5,043,432 | A | 8/1991 | Dilling |
| 5,411,594 | A | 5/1995 | Brelsford |
| 6,022,419 | A | 2/2000 | Torget et al. |
| 6,228,177 | B1 | 5/2001 | Torget |
| 6,409,841 | B1 | 6/2002 | Lombard |
| 6,419,788 | B1 | 7/2002 | Wingerson |
| 8,317,928 | B1 | 11/2012 | Iyer et al. |
| 2006/0188965 | A1 | 8/2006 | Wyman et al. |
| 2006/0286628 | A1 | 12/2006 | Everett et al. |
| 2007/0267008 | A1 | 11/2007 | Funazukuri et al. |
| 2008/0044877 | A1 | 2/2008 | Penttila et al. |
| 2008/0057555 | A1 | 3/2008 | Nguyen |
| 2008/0064906 | A1 | 3/2008 | Foody et al. |
| 2008/0121359 | A1 | 5/2008 | Holtzapple et al. |
| 2010/0048884 | A1 | 2/2010 | Kilambi |
| 2010/0063271 | A1 | 3/2010 | Allan et al. |
| 2010/0175690 | A1 | 7/2010 | Nagahama et al. |
| 2010/0184176 | A1* | 7/2010 | Ishida ............... B01D 11/0226 435/165 |
| 2010/0313882 | A1 | 12/2010 | Dottori et al. |
| 2011/0179703 | A1 | 7/2011 | Gupta et al. |
| 2012/0282465 | A1 | 11/2012 | Kadam et al. |
| 2013/0171709 | A1 | 7/2013 | Kusuda et al. |
| 2014/0030524 | A1 | 1/2014 | Kadam et al. |

FOREIGN PATENT DOCUMENTS

| | | |
|---|---|---|
| CA | 2816250 | 10/2011 |
| CN | 101613377 | 12/2009 |
| CN | 101709227 A | 5/2010 |
| CN | 101851688 | 10/2010 |
| CN | 101851688 A | 10/2010 |
| CN | 102071040 A | 5/2011 |
| CN | 201180060121.X | 10/2011 |
| EP | 1076042 A1 | 2/2001 |
| EP | 1561730 A1 | 8/2005 |
| EP | 1716920 | 11/2006 |
| EP | 1716920 A1 | 11/2006 |
| EP | 2075347 | 7/2009 |
| EP | 11838318.1 | 10/2011 |
| EP | 13784501.1 | 4/2013 |
| GB | 2100282 A | 12/1982 |
| IN | 4852/DELNP/2013 | 10/2011 |
| JP | 2001262162 A | 9/2001 |
| JP | 2001-300486 A | 10/2001 |
| JP | 2005081332 A * | 3/2005 |
| JP | 2007111673 A | 5/2007 |
| JP | 2009178657 A | 8/2009 |
| JP | 2009183806 | 8/2009 |
| JP | 4699566 B1 | 6/2011 |
| KR | 100904561 | 6/2009 |
| KR | 10-2013-7014046 | 10/2011 |
| SE | 1051145-9 | 11/2010 |
| SE | 1150059-2 | 1/2011 |
| WO | WO 2008/121043 | 10/2008 |
| WO | WO 2011/091044 A1 | 7/2011 |
| WO | WO-2011/094859 A1 | 8/2011 |
| WO | PCT/SE2011/051292 | 10/2011 |
| WO | WO-2012/042840 A1 | 4/2012 |
| WO | WO 2012/141652 | 10/2012 |
| WO | WO-2013/013318 A1 | 1/2013 |
| WO | WO 2013/070160 | 5/2013 |
| WO | WO 2013/165308 | 11/2013 |
| WO | WO 2014/074066 | 5/2014 |

OTHER PUBLICATIONS

Mosier et al, Features of promising technologies for pretreatment of lignocellulosic biomass, 2005, bioresource technology, 96, pp. 673-686.*

English translation of JP2005081332, 2005.*

Holladay et al , 2007, Top Value-Added Chemicals from Biomass vol. II—Results of Screening for Potential Candidates from Biorefinery Lignin.*

Sakaki et al, Decomposition of Cellulose in Near-Critical Water and Fermentability of the Products, 1996, energy fuels, 10 (3) pp. 684-688.*

Ehara et al, A comparative study on chemical conversion of cellulose between the batch-type and flow-type systems in supercritical water, 2002, cellulose, vol. 9, issue 3-4, pp. 301-311.*

Yu et al, Some Recent Advances in Hydrolysis of Biomass in Hot-Compressed Water and Its Comparisons with Other Hydrolysis Methods, 2008, energy fuels, 22(1), pp. 46-60.*

Hendriks, et al., "Pretreatments to enhance the digestibility of lignocellulosic biomass", Bioresource Technology, vol. 100, (2009) (pp. 10-18).

Non-Final Office Action issued on Dec. 3, 2015 for U.S. Appl. No. 14/441,427, filed May 7, 2015 and published as US-2015-0292049-A on Oct. 15, 2015 (Applicant—Renmatix, Inc. // Inventor—Carlius, et al.) (19 pages).

Non-Final Office Action issued on Nov. 9, 2015 for U.S. Appl. No. 14/397,805, filed Oct. 29, 2014 and published as US-2015-0122245-A1 on May 7, 2015 (Applicant—Renmatix, Inc. // Inventor—Johannesson, et al.) (18 pages).

Non-Final Office Action issued on Oct. 27, 2015 for U.S. Appl. No. 14/356,388, filed May 5, 2014 and published as US 2014-0323716 A1 on Oct. 30, 2014 (Applicant—Renmatix, Inc. // Inventor—Carlius, et al.) (25 pages).

Final Office Action issued on Mar. 3, 2016 for U.S. Appl. No. 14/356,388, filed May 5, 2014 and published as US 2014-0323716 A 1 on Oct. 30, 2014 (Applicant—Renmatix, Inc. // Inventor—Carlius, et al.) (19 pages).

First Office Action issued by the State Intellectual Property Office of the People's Republic of China for application CN 201380022618.1 (Applicant—Renmatix, Inc.) (Original—16 pages // Translation—6 pages).

Final Office Action issued on Mar. 25, 2016 for U.S. Appl. No. 14/397,805, filed Oct. 29, 2014 and published as US-2015-0122245-A 1 on May 7, 2015 (Applicant—Renmatix, Inc. // Inventor—Johannesson, et al.) (21 pages).

Chen et al., Transformation of Lignocellulose to Produce Fuel Ethanol, "Straw Resource High Ecological Value Theory and Application", Beijing Chemical Industry Press, Sep. 2006, 1st Edition,

(56) References Cited

OTHER PUBLICATIONS pp. 166-170, Section 4.3.1.2 and Section 4.3.1.4 (Original—6 pages // English Language Abstract and Table of Contents—3 pages).
Extended European Search Report issued on Jan. 8, 2016 for application EP 13784501.2, filed on Apr. 30, 2013 and published as EP 2844777 on Mar. 11, 2015 (Applicant—Renmatix, Inc. // Inventor—Johannesson, et al.) (8 pages).
Extended European Search Report issued on Aug. 29, 2014 for application EP 12771085.3, filed on Apr. 13, 2012 and published as EP 2697380 on Feb. 19, 2014 (Applicant—Renmatix, Inc.) (7 pages).
Toor, et al., "Hydrothermal liquefaction of biomass: a review of subcritical water technologies," Energy vol. 36, pp. 2328-2342 (2011).
Office Action issued Apr. 13, 2011 by the Swedish Patent Office for Application No. 1051145-9, which was filed Nov. 11, 2010. (Applicant—Reac Fuel Ab//1st Named Inventor—Eckman) (11 pages).
International Type Search Report issued Apr. 13, 2011 for Application No. 1051145-9, which was filed Nov. 11, 2010 (Applicant—Reac Fuel Ab//1st Named Inventor—Eckman) (8 pages).
Search Report for PCT Patent Application No. PCT/SE2011/051292 issued Jan. 19, 2012.
Matsunaga et al. "Super-Rapid Chemical Conversion of Sugi Wood by Supercritical and Subcritical Water Treatment". In: Mokuzai Gakkaishi, 2004, vol. 50, No. 5, pp. 325-332.; abstract; figures 1-9.
Sakaki et al. "Decomposition of Cellulose in Near-Critical Water and Fermentability of the Products". In: Energy and Fuels, 1996, vol. 10, pp. 684-688.
Allen et al. "Fractionation of Sugar Cane with Hot, Compressed, Liquid Water". In: Industrial & Engineering Chemistry Research, 1996, vol. 35, pp. 2709-2715.
Liu et al. "Partial flow of compressed-hot water through corn stover to enhance hemicellulose sugar recovery and enzymatic digestiility of cellulose". In: Bioresource Technology, 2005, vol. 96, pp. 1978-1985.
Hashaikeh et al. "Hydrothermal dissolution of willow in hot compressed water as a model for biomass conversion". In:Fuel, 2007, vol. 86, pp. 1614-1622.
Phaiboonsilpa et al. "Two-step hydrolysis of japanese cedar as treated by semi-flow hot-compressed water". In: Journal of Wood Science, 2010, vol. 56, pp. 331-338.
Yu et al. "Some recent advances in hydrolysis of biomass in hot-compressed water and its comparisons with other hydrolysis methods". In: Energy & Fuels, 2008, vol. 22, pp. 46-60.
Ehara et al. "A comparative study on chemical conversion of cellulose between the batch-type and flow-type systems in supercritical water". In: Cellulose, 2002, vol. 9, pp. 301-311.
Allen, S. G. et al. "Fractionation of Sugar Cane with Hot, Compressed, Liquid Water". In: Industrial & Engineering Chemistry Research, 1996, vol. 35, pp. 2709-2715.
Ehara, K. et al. "A comparative study on chemical conversion of cellulose between the batch-type and flow-type systems in supercritical water". In: Cellulose, 2002, vol. 9, pp. 301-311.; abstract; figure 1; table 1.
Hashaikeh, R. et al. "Hydrothermal dissolution of willow in hot compressed water as a model for bio mass conversion". In: Fuel, 2007, vol. 86, pp. 1614-1622.
Lilt, C. et al. "Partial flow of compressed-hot water through corn stover to enhance hemicellulose sugar recovery and enzymatic digestiility of cellulose". In: Bioresource Technology, 2005, vol. 96, pp. 1978-1985.; paragraphs 2.2, 3.4, table 1.
Matsunaga, M. et al. "Super-Rapid Chemical Conversion of Sugi Wood by Supercritical and Subcritical Water Treatment". In: Mokuzai Gakkaishi, 2004, vol. 50, No. 5, pp. 325-332.
Phaiboonsilpa, N. E al. "Two-step hydrolysis of japanese cedar as treated by semi-flow hot-compressed water". In: Journal of Wood Science, 2010, vol. 56, pp. 331-338.
Sakaki, T. el al. "Decomposition of Cellulose in Near-Critical Water and Fermentability of the Products". In: Energy and Fuels, 1996, vol. 10, pp. 684-688.
Yu, Y. et al. "Some recent advances in hydrolysis of biomass in hot-compressed water and its comparisons with other hydrolysis methods". In: Energy & Fuels, 2008, vol. 22, pp. 46-60.
Written Opinion and International Search Report mailed Jan. 19, 2012 for Application No. PCT/SE2011/051292, which was filed Oct. 28, 2011 and published as WO 2012/060767 (Applicant—Reac Fuel Ab//1st Named Inventor—Eckman) (13 pages).
International Preliminary Report on Patentability issued Dec. 15, 2011 for Application No. PCT/SE2012/051292, which was filed Oct. 28, 2011 and published as WO 2012/060767 (Applicant—Reac Fuel Ab//1st Named Inventor—Eckman) (8 pages).
International Search Report mailed by the International Searching Authority on Feb. 19, 2013 for application PCT/SE2012/051215, filed on Nov. 6, 2012, and published as WO 2013/070160 on May 16, 2013 (Inventor—Carilus, et al // Applicant—Renmatix, Inc.) (5 pages).
Written Opinion mailed by the International Searching Authority on Feb. 19, 2013 for application PCT/SE2012/051215, filed on Nov. 8, 2012, and published as WO 2013/070160 on May 16, 2013 (Inventor—Carilus, et al // Applicant—Renmatix, Inc.) (7 pages).
International Search Report mailed by the International Searching Authority on May 7, 2012 for application PCT/SE2013/050406, filed on Apr. 13, 2012, and published as WO 2012/141652 on Oct. 18, 2012 (Inventor—Carilus, et al // Applicant—Renmatix, Inc.) (5 pages).
Written Opinion mailed by the International Searching Authority on May 15, 2014 for application PCT/SE2013/051324, filed on Nov. 8, 2013, and published as WO 2014/074066 A1 on May 15, 2014 (Inventor—Carilus, et al // Applicant—Renmatix, Inc.) (5 pages).
International Search Report mailed by the International Searching Authority on Aug. 27, 2013 for application PCT/SE2013/050478, filed on Apr. 30, 2013, and published as WO/2013/165308 A1 onNov. 7, 2013 (Inventor—Johannesson et al // Applicant—Renmatix, Inc.) (5 pages).
Written Opinion mailed by the International Searching Authority on Aug. 27, 2013 for application PCT/SE2013/050478, filed on Apr. 30, 2013, and published as WO/2013/165308 A1 onNov. 7, 2013 (Inventor—Johannesson et al // Applicant—Renmatix, Inc.) (6 pages).
International Search Report mailed by the International Searching Authority on May 15, 2014 for application PCT/SE2013/051324, filed on Nov. 8, 2013, and published as WO 2014/074066 A1 on May 15, 2014 (Inventor—Carilus, et al. // Applicant—Renmatix, Inc.) (5 pages).
Written Opinion mailed by the International Searching Authority on May 15, 2014 application PCT/SE2013/051324, filed on Nov. 8, 2013, and published as WO 2014/074066 A1 on May 15, 2014 (Inventor—Carilus, et al // Applicant—Renmatix, Inc.) (5 pages).
Extended European Search Report issued on May 25, 2016 by the European Patent Office for Application No. 13853191.8 (Inventor—Anders Carlius et al) (8 Pages).
Extended European Search Report issued on Jun. 29, 2015 for application EP 11284740.0 (Applicant—Renmatix, Inc.) (7 pages).
Final Office Action issued on Nov. 28, 2016 for U.S. Appl. No. 14/356,388, filed May 5, 2014 and published as US 2014-0323716 A1 on Oct. 30, 2014 (Applicant—Renmatix, Inc.// Inventor—Carlius, et al.) (23 pages).
Non-Final Office Action issued on Aug. 10, 2016 for U.S. Appl. No. 14/356,388, filed May 5, 2014 and published as US 2014-0323716 A1 on Oct. 30, 2014 (Applicant—Renmatix, Inc. // Inventor—Carlius, et al.) (22 pages).
Non-Final Office Action issued on Jul. 28, 2016 for U.S. Appl. No. 14/441,427, filed May 7, 2015 and published as US-2015-0292049-A on Oct. 15, 2015 (Applicant—Renmatix, Inc. // Inventor—Carlius, et al.) (17 pages).
Non-Final Office Action issued on Feb. 2, 2017 for U.S. Appl. No. 14/441,427, filed May 7, 2015 and published as US-2015-0292049-A on Oct. 15, 2015 (Applicant—Renmatix, Inc. //Inventor—Carlius, et al.) (18 pages).
Oh, H., et al., "Evaluation of PAC Behavior and Fouling Formation in an Integrated PAC-UF Membrane for Surface Water Treatment," Desalination 192(1-3):54-62, May 2006.

(56) References Cited

OTHER PUBLICATIONS

Yoshida, H. et al: "Efficient, high-speed methane fennentation for sewage sludg eusing subcritical water hydrolysis as pretreatment", Bioresource Technology, 2009, vol. 100, 2933-2939.
Phaiboonsilp A, N. et al. "Effect of acetic acid addition on chemical conversion of woods as treated by semi-flow hot-compressed water". In:Holzforschung, 2011, vol. 65, pp. 667-672.
Phaiboonsilp A, N. et al. "Two-step hydrolysis of nip a (Nypa fruticans) frond as treated by semi-flow hot-compressed water". In: Holzforschung, 2011, vol. 65, pp. 659-666.
Kumagai, S. et al. "Fractionation and solubilization of cellulose in rice hulls byhot-compressed water treatment, and production of glucose from the solubilizedA . . . II. products by enzymatic saccharification". In: Kagaku Kogaku Ronbunshu, 2008, vol. 34, m. 4, pp. 458-462 Abtract Only.
Watanabe et al.Glucose reactions with acid and base catalysts in hot compressed water at 473K. Carbohydrate Research, v 340, pp. 1925-1930, 2005.
U.S. Appl. No. 61/409,269, filed Nov. 2, 2010, Ekman.
Extended European Search Report dated Aug. 29, 2014 for application EP 12771085.3, filed on Apr. 13, 2012 and published as EP 2697380 on Feb. 19, 2014 (Applicant—Renmatix, Inc.) (7 pages).
Supplementary European Search Report dated Jun. 7, 2017 by the European Patent Office for Application No. 11838318.1, which was filed on Oct. 28, 2011 and published as 2635713 on Sep. 11, 2013 (Applicant—Renmatix, Inc.) (8 Pages).

\* cited by examiner

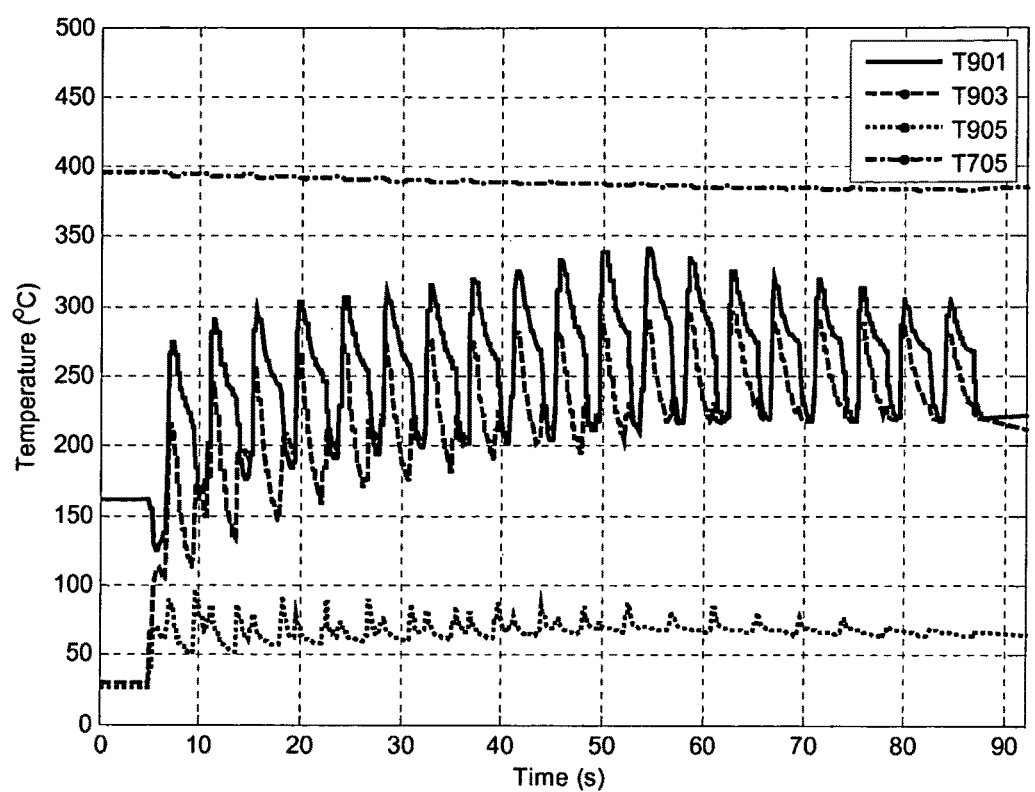
Fig. 1. Batch experiment.

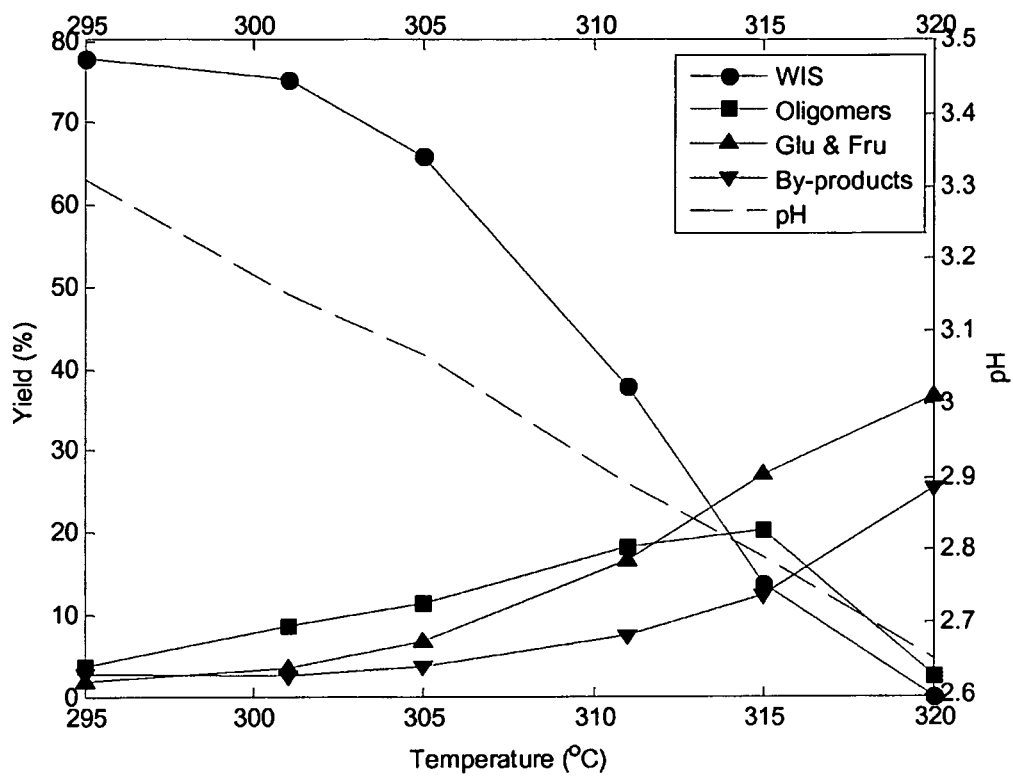
Fig. 2. Flow experiment
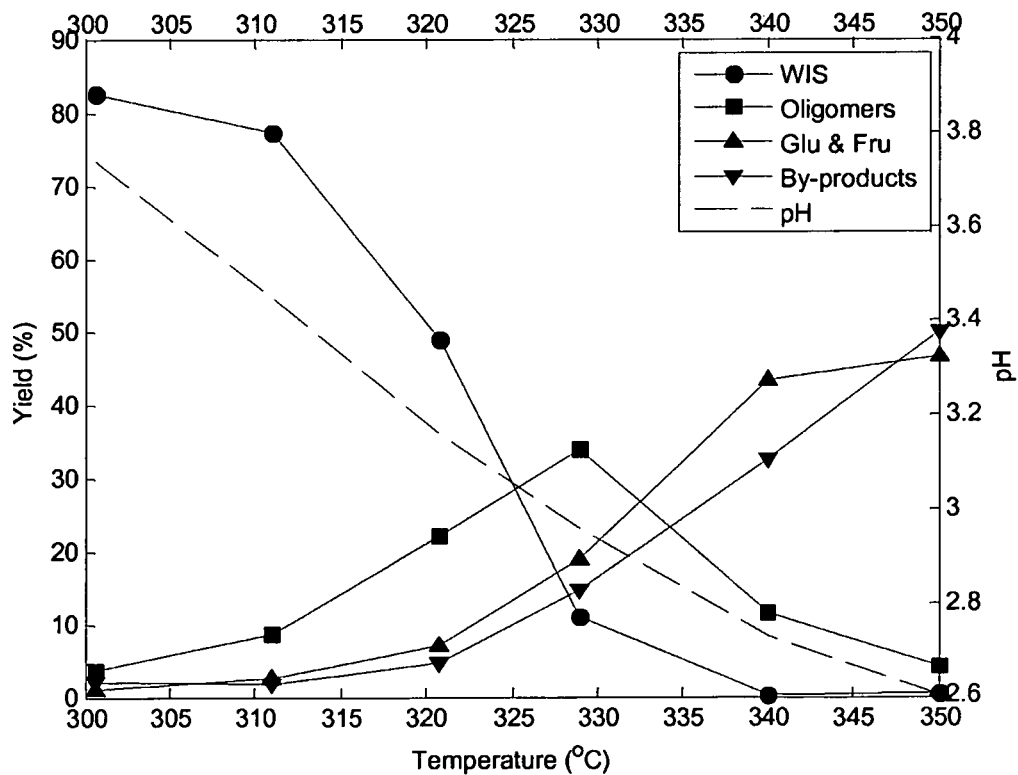
Fig. 3. Flow experiment

PROCESS FOR CONTROLLED LIQUEFACTION OF A BIOMASS FEEDSTOCK BY TREATMENT IN HOT COMPRESSED WATER

FIELD OF INVENTION

The present invention relates to a process for a controlled conversion of a biomass feedstock.

TECHNICAL BACKGROUND

Different processes for converting biomass in sub- or super-critical conditions are known. E.g. US2010/0175690 describes a method and system for hydrolyzing cellulose and/or hemicellulose contained in a biomass into monosaccharides and oligosaccharides by using high-temperature and high-pressure water in a subcritical condition. The process involves a temperature lowering step after the hydrolyzing step as means for preventing saccharides from degrading. The hydrolyzing step for hemicellulose is performed in a temperature of between 140° C. and 180° C. and for cellulose in a temperature of between 240° C. and 280° C., optionally in a two step-process.

Moreover, in "Chemical conversion of wood by treatment in a semi-batch reactor with subcritical water", Matsunaga et al., The Journal of Supercritical Fluids 44 (2008) 364-369, it is disclosed a process where sugi wood meal is extracted with subcritical water in a semi-batch reactor. The preheated water used is continuously supplied through a reactor containing the wood meal. Water-soluble compounds which are produced by hydrolysis and/or pyrolysis leave the reactor as aqueous solution and are cooled in a heat exchanger as to prevent further decomposition. In the process above, the reactor is pre-heated to 160° C. and water in subcritical condition (260-360° C., 15-25 MPa) is supplied.

Furthermore, in "Fractionation of Sugar Cane with Hot Compressed, Liquid Water", Industrial Engineering Chemistry Research, 1996, vol 35. Page 2709-2715, Allen, S. G. et al, there is disclosed the fractionation of sugar-cane bagasse and leaves by a rapid (45 s to 4 min) immersed percolation using only hot (190-230° C.) water. Over 50% of the biomass is said to be solubilized.

In "Partial flow of compressed-hot water through corn stover to enhance hemicellulose sugar recovery and enzymatic digestibility of cellulose". Bioresource Technology, 2005, vol. 96, page 1978-1985, Liu, C. et. Al, there is disclosed a flow-through pretreatment with compressed-hot water where compressed-hot water is applied at 200° C. Partial flow is said to reduce water consumption by 60% compared with continuous flowthrough operation and higher xylose sugar yields (84-89%) compared to batch pretreatment (46.6%) was achieved.

Moreover, in US 2010184176 A1, there is disclosed a biomass hydrothermal decomposition apparatus, method thereof and organic material production system using biomass material. In the method disclosed, hot compressed water and biomass material is counter-currently fed to each other, lignin and hemicellulose is separated from the biomass material, and the reaction is performed at 180-240° C.

Furthermore, in US 2010063271 A1, there is shown a supercritical fluid biomass conversion system and method thereof, for converting biomass material into fermentable sugars and aromatic substances.

In "Decomposition of Cellulose in Near-Critical water and Fermentability of the Products" Energy and Fuels, 1996, vol. 10, page 684-688, Sakaki T. et. al, there is discussed and evaluated the non-catalytic decomposition characteristics of cellulose in near-critical water by heating a sealed reactor in which the cellulose and water were charged in a salt bath kept at 305, 355, or 405° C. Cellulose is said to rapidly decompose to water solubles (WS), and the WS is further decomposed after the WS yield reached nearly 80%. The heating time giving the maximum WS yield was shortened to below 15 s by increasing the treatment temperature to over 355° C.

Moreover, in "Hydrothermal dissolution of willow in hot compressed water as a model for biomass conversion", Hashaikeh, R. et al, dissolution of willow as a model system for biomass conversion was investigated in the 200-350° C. temperature range. The dissolution process was studied using a batch-type (diamond-anvil cell) and a continuous flow process reactor. A 95% dissolution of willow was achieved. The lignin and hemicellulose in willow were fragmented and dissolved at a temperature as low as 200° C. and a pressure of 10 MPa. Cellulose dissolved in the 280-320° C. temperature range.

Furthermore, in "Two-step hydrolysis of Japanese cedar as treated by semi-flow hot-compressed water", Phaiboonsilpa, N. et. al, two-step hydrolysis of Japanese cedar (*Cryptomeria japonica*) was studied as treated by semi-flow hot-compressed water at 200° C./10 MPa for 15 min and 280° C./10 MPa for 30 min as the first and second stages, respectively.

In CN101851688, there is disclosed a semi-continuous reaction device for independent dissolution and hydrolysis of biomass by hydro-thermal treatment. Furthermore, in CN101613377, there is shown a biomass supercritical and subcritical combined continuous type pretreatment and hydrolysis equipment and a method thereof.

Moreover, in "A comparative study on chemical conversion of cellulose between the batch-type and flow-type systems in supercritical water", Ehara, K. Et al, microcrystalline cellulose (avicel) was treated in supercritical water using batch-type and flow-type system.

Furthermore, in EP1716920, there is disclosed a method of and an apparatus for continuous subcritical water decomposition treatment of material to be processed containing solid matter, which is said to be capable of controlling decomposition reaction of the material to be processed and suitable for large-scale operations.

The present invention is directed at providing a process concept for the conversion of biomass, which process concept is optimal in terms of providing high value end products in a resource effective and thus economically favourable way. Furthermore, the present invention is directed to providing optimal process conditions for the processing of biomass material in HCW (hot compressed water) at sub- and/or subcritical conditions, so that high yields are obtainable for said high value end products.

SUMMARY OF INVENTION

The stated purpose above is achieved by a process for a controlled conversion of a biomass feedstock, wherein the process comprises the steps of:
- loading the biomass feedstock to at least one reactor;
- liquefaction of the biomass feedstock into a monomer and/or oligomer sugar mixture in said reactor by treatment in hot compressed liquid water (HCW) at sub- and/or super-critical condition; and
- removal of the monomer and/or oligomer sugar mixture, being the product molecules, to avoid continued detrimental decomposition, and wherein the liquefaction is performed in a temperature of at least 280° C. during a time of from 1.5 to 30 s.

As may be seen above, the preferred process conditions stated in the process according to the present invention are not shown or hinted in the documents discussed above. In "Fractionation of Sugar Cane with Hot Compressed, Liquid Water", the temperature used is lower and the percolation time longer. Moreover, the produced glucose is bonded in solid chains, however according to the present invention, a water soluble monomer and/or oligomer sugar mixture is produced. Also in "Partial flow of compressed-hot water through corn stover to enhance hemicellulose sugar recovery and enzymatic digestibility of cellulose", the temperature used is much lower and the intended final product is bonded glucose. Moreover, in US 2010184176 A1, the used temperature is 180-240° C. and the reaction time is above 3 min, which differs considerably in comparison to the present process.

In the case of US 2010063271 A1, this document is directed to a method where biomass is converted to fermentable sugars and aromatic substances, however at least not directly a soluble monomer and/or oligomer sugar mixture comprising water soluble monomers and oligomers. Furthermore, in US 2010063271 it is described how to heat the water laden biomass material to gain energy to a temperature of at least 374.4° C. and for a period of time that preferably ranges from about 0.4 to about 10 seconds, however this is not related to the actual reaction time for the liquefaction. Any such time is not disclosed for the operation discussed in US 2010063271.

Moreover, in "Decomposition of Cellulose in Near-Critical water and Fermentability of the Products", a batch process in a sealed vessel is discussed for different temperatures (205-405° C.). First of all, the optimal conditions are not disclosed in the article in relation to the temperature. Moreover, the intended reaction times are not shown to be in the range as according to the present invention. In the article short reaction times are suggested when very high temperatures are used, as the articles states that the heating time giving the maximum yield was shortened to below 15 s by increasing the treatment temperature to over 355° C. It should also be said that the articles does not disclose any clear information regarding how and when to remove the monomer and/or oligomer sugar mixture to avoid continued detrimental decomposition.

Furthermore, in "Hydrothermal dissolution of willow in hot compressed water as a model for biomass conversion", a temperature range of 200-350° C. is used, however it does not suggest any minimum temperature of 280° C., such as according to the present invention, and does not suggest the combination of such temperature and short reaction times, such as according to the present invention. Also in "Two-step hydrolysis of Japanese cedar as treated by semi-flow hot-compressed water", no reaction having such a short reaction time is used or suggested.

Furthermore, in both CN101851688 and CN101613377, there is not disclosed a reaction with reaction times such as according to the present invention. Moreover, the minimum temperature of 280° C. is not suggested. Also in "A comparative study on chemical conversion of cellulose between the batch-type and flow-type systems in supercritical water", it should be noted that the short times of seconds discussed in this article (see FIG. 2) are related to times during changes of the temperature and pressure inside the reaction vessel of a batch-type and flow type system, respectively, in a reaction temperature which is extremely high, namely 380° C. Such high temperatures are not preferred according to the present invention. According to the present invention, temperatures in the range of 280-374° C. are preferred. Therefore, according to one preferred embodiment, the liquefaction according to the present invention is performed at a sub-critical condition implying a temperature of below 374° C. According to the invention, it has been proven that it is possible to increase the control of the decomposition of the biomass feedstock if a temperature in the sub-critical range for HCW is used. The temperature should of course be high enough (at least 280° C.) to drive the reaction, however still in the sub-critical area (below 374° C.). To "control the decomposition" should, as is explained below, be interpreted as driving the liquefaction towards high yields of desired components in the monomer and oligomer mixture. As is seen in the examples and figures, such high yields are obtained in the sub-critical temperature range.

Furthermore, in relation to EP1716920, the process disclosed therein is very different from the present invention. This is inter alia seen from the figures in EP1716920, where the residence times of several minutes are shown.

SHORT DESCRIPTION OF THE DRAWINGS

In FIG. 1 there is shown different temperatures vs. time and hence the pulse temperature profile for a batch process according to the present invention.

In FIG. 2 there is shown the temperature, pH value and yield of different relevant components during a flow experiment of the present invention.

In FIG. 3 there is shown the temperature, pH value and yield of different relevant components during another flow experiment of the present invention.

SPECIFIC EMBODIMENTS OF THE INVENTION

Below, specific embodiment of the present invention are disclosed. As may be noted from above, the temperature range as well as the reaction time, or residence time for the increased temperature, are important parameters according to the present invention. According to one specific embodiment, the temperature is in the range of 280-350° C. It should be noted that the temperature profile within the temperature range may vary. One example is a temperature profile where the temperature is increased to at least 280° C. and then hold constant for from 1.5 to 30 s and then the temperature is decreased below 280° C. The temperature drop after the residence time over 280° C. may also have different profiles, e.g. a rapid decrease so that continued decomposition of the produced water soluble monomers and oligomers is avoided. Another temperature profile may involve a temperature increase from 280° C. to a temperature peak at 350° C. or below, then being followed of a temperature decrease, said increase and decrease being performed within the residence time of from 1.5 to 30 s. It should also be noted that the temperature increase and decrease may have steep curves so that an increase up to for instance 300° C. is made very quickly, the temperature is then hold almost constant, and then the decrease to a temperature below 280° C. is also made very rapidly. Also in this case, the temperature above 280° C. is only held for a maximum time of 30 seconds according to the present invention.

The preferred temperature profile according to the present invention depends on the biomass starting material being used and also the intended monomer and oligomer mixture being produced. In this sense it should also be mentioned that outside the temperature profile during the actual reaction according to the present invention, the temperature should preferably be held at a maximum of 200° C., preferably well below that temperature, to avoid decomposition of the monomers.

According to yet another specific embodiment of the present invention, the temperature is in the range of 300-350° C.

The process set-up according to the present invention may vary. All of a batch mode, semi-batch mode and flow mode may be used according to the present invention. This also implies that the loading of the biomass starting material as well as the loading or injection of HCW may be performed by different means. In this sense it should also be noted that the biomass feedstock may also have been pretreated before the process according to the present invention. This may for instance be of interest to liquefy and separate hemicelluloses in the biomass at lower temperature before the process, or for instance for separating away lignin in a lignocellulosic biomass starting material.

Below, different set-up embodiments according to the present invention are discussed.

According to one embodiment of the present invention, loading of the biomass feedstock is performed by preloading biomass into a batch reactor, HCW is injected to the batch reactor by one cycle or repeated cycles, and solubilized material is discharged from the batch reactor after a reaction time t. According to this embodiment, the process of the invention is performed batch-wise, meaning that the loading is performed batchwise but the HCW flow is pulsed. First solid lignocellulosic biomass is loaded to the batch reactor and then the actual liquefaction is performed by injection of HCW to the batch reactor. The liquefaction reaction may be performed by only adding HCW once or as repeated cycles. During each cycle the water is allowed to react with the biomass, and is subsequently discharged from the reactor. Regardless of one or several cycles, a reaction time t, in the order of a few seconds (e.g. up to 15 seconds, or a maximum of 30 seconds), is decided for the liquefaction process after which solubilized material is discharged from the batch reactor. Possible non-dissolved (non-reacted) solid biomass feedstock is kept inside of the batch reactor, i.e. only the solubilized material which is the aqueous monomer and/or oligomer sugar mixture is discharged from the batch reactor. E.g. a filter may prevent solid, un-dissolved material, from leaving the reactor.

According to another embodiment of the present invention, loading of the biomass feedstock is performed by cyclic loading of biomass into a single batch reactor or into a series of batch reactors, said reactors being coupled in series or parallel, so that said reactor(s) is refilled after complete biomass liquefaction, HCW is injected to the batch reactor or series of batch reactors by one cycle or by repeated cycles, and solubilized material is discharged from the batch reactor after a reaction time t. This is an extension of the embodiment of the present invention disclosed above, whereby the reactor is cyclically refilled after complete biomass dissolution. This could e.g. be performed by suction, a feeder screw or by other means. In another version of this embodiment the reactor is replaced by a second pre-loaded reactor, which is subsequently replaced by a third and so on. The pre-loading of the reactors could be performed cyclically in a carousel fashion with the new loaded reactors returning to processing step, or off-line batch-wise.

Both diffusion of HCW molecules into the biomass start material and reaction time are important parameters affecting the process according to the present invention. Therefore, the timing of discharging the end-product mixture from the batch reactor, and hence setting the reaction time t, is important to the embodiments of the present invention disclosed above. If the reaction time is set too short, the conversion is not made enough to obtain a high yield of desirable monomers and oligomers, and if the reaction time is set too long, too high percentage of the monomers have further degraded into other end molecules, i.e. so called continued detrimental decomposition has resulted.

According to one embodiment of the present invention, separation of a lignin component is performed by filtration/removal of non-solubilized material from the batch reactor or series of batch reactors.

According to yet another embodiment, loading of the biomass feedstock is performed by cyclic loading of biomass into at least one flow reactor, HCW is injected to said flow reactor by one cycle, and solubilized material is flowed downstreams from the flow reactor to a non-reactive zone. This is a modification of the embodiment described above, where the batch reactor is replaced by a flow reactor, e.g. a tube reactor. Instead of allowing for a reaction time for the biomass and water inside the closed (flow free) reactor, the reaction takes place in a tube with flowing water. At the entrance of the reactor is a volume for (cyclically) filling of biomass. Super/sub-critical water is injected into the filling volume which dissolves the biomass to small fragments that subsequently may pass through a suitable filter and enter the flow reactor (tube). Inside the flow reactor the fragments/polymers of cellulose continue to break down to oligo- and/or monomers. Preferably there is a temperature gradient in the flow reactor that is optimized for breaking the cellulose components down to suitable oligo- and/or monomers. A set-up where the process according to the present invention may be performed continuously, such as by use of a flow reactor, e.g. a tube reactor, have proven to be a very effective way. Such a set-up mode is therefore preferred. Moreover, in relation to the continuous flow set-up embodiment according to the present invention it should be noted that also this system may be said to be driven with temperature pulses, as discussed below, however in this case each pulse should be seen as a rapid increase and decrease in temperature due to the transition of the flow through a high temperature region.

A non-reactive zone may be seen as a quenching zone, i.e. a zone where no further or substantially no further decomposition of the biomass occurs. This zone is preferably held below 200° C.

Optionally several flow reactors can be used, for instance two reactors out of sync, where loading of biomass is performed in one reactor while the reaction is performed in a second reactor, thus enabling a continuous net flow. Therefore, according to one embodiment, several flow reactors are used and at least one flow reactor is a loading reactor and at least one flow reactor is a reaction reactor.

According to a further embodiment of the present invention, loading of the biomass feedstock is performed by continuous loading of biomass into at least one flow reactor, HCW is continuously injected to said flow reactor, and solubilized material is flowed downstreams from the flow reactor to a non-reactive zone. According to this embodiment, solid (lignocellulosic) biomass is continuously fed into a reactor, by a feeder screw or by other means, while at the same time super/sub-critical water is continuously pumped into the same reactor.

According to yet another specific embodiment of the present invention, the biomass feedstock is a slurry which is continuously loaded to a flow reactor, said slurry is rapidly warmed to sub- or super-critical condition, and solubilized material is flowed downstreams from the flow reactor to a non-reactive zone. The slurry is pumped at high pressure through a heating region where it is exposed to temperatures that bring the water to super/sub-critical conditions. Preferably this region is designed so that optimal thermal contact is achieved, e.g. by increasing the contact surface between the slurry and the boundaries of the heating region. Preferably the heating region has a temperature profile in order to optimize oligo- and/or monomers yields. The residence time of the slurry in the heating region should be of the order of e.g. a few seconds.

As is described above, all of the biomass feedstock is often not liquefied in one process loop according to the present invention. Therefore, it is of interest to make sure to handle non-solubilized start material during the process. According to one specific embodiment of the present invention, the process also comprises the step of removal of non-solubilized material. This may e.g. be made by filtration which has been hinted above. Moreover, according to one embodiment of the invention, the removed non-solubilized material is reprocessed. Such reprocessing may either be made back to the same reactor or in fact to another reactor. In the latter case, it is easier to design a process where two different temperature ranges are used if this is of interest for the liquefaction process. This depends of course on inter alia the biomass start material. The inventors have found out, e.g. when using pine as a starting material, that it is possible to achieve a yield of at least 20% with reference to the yield of glucose, and a total monomeric sugar yield of at least 30%, 35% or even 40%, by the liquefaction process according to the present invention.

According to another specific embodiment of the present invention, lignin is separated at the step of removal of non-solubilized material. The aim is to separate lignin from e.g. a lignocellulosic biomass, so that it could potentially be further processed to valuable chemicals.

The process according to the present invention is preferably performed free from any chemicals besides HCW and the biomass feedstock. It should be noted that, there are additives that may be of interest for the present invention. One example is acids, such as e.g. organic acids, but also inorganic acids. Such acids may drive the liquefaction process so that a comparatively lower temperature may be used. Therefore, according to one embodiment of the present invention, one pH lowering additive, such as an acid, is added to the process, suitably before but in close connection to the temperature increase. Nevertheless, the process according to the present invention is intended to be performed in HCW as the main solvent held at sub- or super-critical condition, i.e. neither e.g. alcohols nor carbon dioxide should be used. The actual process conditions may vary according to the present invention. According to one specific embodiment, each injection of HCW implies applying a temperature pulse at a sub- or super-critical condition in the reactor to allow for liquefaction of the biomass feedstock, said pulse involving applying a pulse start temperature during a temperature increase time and allowing for liquefaction reaction to occur during the reaction time t. The pulse approach according to the present invention is an effective method for liquefaction of many different biomasses, such as biomasses based on softwood, such as e.g. pine or spruce, or on hardwood, such as e.g. birch. Other start materials are also possible, such as e.g. hemp. In relation to the pulse approach, it should once again be said that this approach may be applied both for a batch process and a continuous flow process according to the present invention.

According to one specific embodiment according to above, the pulse start temperature is at least 280° C. and the reaction time is set to from 1.5 to 30 s. As has been disclosed above, the process according to the present invention preferably is run without any additives except start material and HCW. If such specific additives are used, a lower temperature profile may be possible. The present invention, however, aims at optimizing the liquefaction in terms of both being economically favourable, that is being energy resource and additive undemanding, as well as exhibiting low environmental impact. According to yet another embodiment, the pulse start temperature is in the range of 300° C.-350° C. and the reaction time is set to from 1.5 to 15 s. The temperature pulse may be applied in different ways, such as disclosed above. The pulse time may be described as comprising a temperature increase time, a reaction time and finally a temperature decrease time, the latter being the decay of the pulse. However, the pulse design may vary according to the present invention. The temperature may e.g. be constantly held within a certain range during the reaction time, however also decreasing temperature profiles during the reaction are possible, such as decrease to a certain level when the reactor is set to be discharged or in fact by self-decay until the reaction dies or self-quenches.

Temperature is a really important parameter for the process. As the process should be run in sub- and/or supercritical conditions, it is however important to understand that the pressure should be held at a level high enough so that the HCW is in liquid form.

Moreover, as said above, a pretreatment of the biomass feedstock may be performed, such as for dissolving hemicellulose, where the temperature used should be about at least 230° C., preferably at least 250° C. For dissolving cellulose with the process according to the present, the temperature should be at least 280° C.

The reaction time may vary according to the present invention, however, the applied pulses do not individually last very long. According to one embodiment of the present invention, the reaction time of the liquefaction is set to from 1.5 to 15 s, and the temperature is above 300° C.

Also the ratio of feedstock input in relation to HCW may be of interest for the process, such as for process economic reasons. For such reasons, the process may preferably be run with at least 10% biomass inflow in relation to total inflow (biomass plus HCW), and it may according to the present invention be possible to have a inflow of biomass of e.g. 15-20% in relation to total inflow. It is, however, important to realize that the process according to the present invention may be performed with much lower input levels of biomass feedstock, such as at 1% or even below 1%, and such operation conditions are of course also contemplated according to the present invention.

The process according to the present invention may also comprise an additional product conversion step. Therefore, according to one specific embodiment of the present invention, the process also comprises a subsequent step, said step being anyone or a combination of hydrolysis or fermentation. The hydrolysis may e.g. be catalytic or enzymatic, and the purpose of such an additional process step according to the present invention is to monomerize the water soluble oligosaccharides into monosaccharides. Also this additional process step is preferably performed free from addition of any chemicals besides the catalyst or enzymes being present in the respectively hydrolysis type. The fermentation may be performed in sequence after an additional hydrolysis or directly on the material achieved from the liquefaction process according to the present invention. An additional fermentation step according to the present invention has the purpose of ethanol production and it is e.g. performed adding yeast cells to the sugar solution achieved according to the present invention. One favourable feature of the invention is the resulting solution after the liquefaction. When fermenting this solution it has been shown that the solution has a very low content or a non-existing content of fermentation inhibitors, which renders the possibility of high yields from a subsequent fermentation process.

Moreover, it is important to understand that different biomass start materials are possible to use according to the present invention. According to one specific embodiment, the biomass feedstock is a lignocellulosic biomass feedstock. As may be understood from above, different types of biomasses are possible to use according to the present invention, however according to one specific embodiment of the present invention a lignin-rich start material is used. In this case, the process is aimed at also recovering or extracting the lignin fraction or component.

Also biomasses having a low lignin content or being lignin free may be used according to the present invention. Such biomasses may e.g. be derived from paper board, carton or paper.

EXAMPLES

The following trials and experiments have been conducted.

Biomass is dissolved using hot compressed water (HCW) in a pulsed semi-batch system. As mentioned above, the principle behind the process in this case is to inject HCW into a reactor pre-loaded with biomass, allow for a limited time of reaction, and subsequently flush out the solubilized material while keeping non-dissolved solid residue in the reactor. This is repeated until the biomass is completely dissolved. No additives or chemicals, other than pure water, are used in the liquefaction process. The main components of the system are i) a boiler for heating up water to sub- or super-critical temperatures, ii) a reactor in which the biomass is loaded and the dissolution takes place, and iii) an expansion vessel where the dissolved biomass is collected.

In this trial, the boiler had a volume of 580 ml and it is typically loaded with 250-300 ml of deionized water (Millipore, 18.2 MΩcm). The water is used as it is, without any modifications such as degassing.

The boiler is placed inside a vertical split tube furnace (Lenton PSC 12/90/600V) which is controlled by an external control unit (Eurotherm 3508P1+2132). In order not to push the safety limit specifications for the boiler tube, the surface temperature was never allowed to exceed 440° C. This limits the heating rate of the loaded water, especially at elevated temperatures close to 400° C. The typical heating time is in the range 40-60 minutes. The boiler temperatures used in this study were in the range 360-415° C., and the resulting pressure was in the range 330-370 bar, depending on the amount of loaded water. The pressure and temperature in the boiler was measured by a pressure transducer and thermocouple and continuously monitored by a computer with reference to their respective safety limits. The reactor was a simple cylindrical tube with an inner diameter of 13.1 mm and a volume of 13 ml. The temperature inside the reactor was not directly measured; instead the temperature is measured before and after the reactor by two thermocouples. This solution was chosen in order to simplify the design of the reactor. In order to confine the solid biomass in the reactor the ends were sealed with triple steel mesh filters; 140 µm at the inlet and 55 µm at the outlet of the reactor.

The reactor was loaded with about 30 pine sticks slightly shorter than the length of the reactor, i.e. approximately 10 cm, with an approximate cross section of 1.5 mm. Using sticks with a larger cross section area results in a reduced degree of dissolution, probably due to the decreased reaction surface area. The typical loaded mass was 3000 mg, resulting in a filling factor of about 50%. The reactor and the tubing between the boiler and the reactor were pre-heated to 200-250° C. using a heating tape (Horst Heating Tape HBS) together with a control unit (Horst Temperature Controller HT30). The reactor region is also thermally insulated using rockwool. The pre-heating was turned on 20-30 minutes before the dissolution process was initiated. The expansion vessel was a 35 kg stainless steel container which was used for collecting the dissolved biomass. The large mass and volume of the vessel allowed for a relatively rapid cooling and reduction of the pressure.

The solution collected in the expansion vessel, typically 200 ml, was brown-colored with particulate material, which after a while sediments left a slightly yellowish top solution. The color of the solution as well as the proportion of the liquid and solid phases varied depending on the process parameters. The smell of the solution resembled that of fresh-cut wood, with the inclusion of a slight tarry smell for the samples that had been exposed to the most extreme reaction time and temperature conditions. The pH of the solution was in the range 3.5-4.0. The solid residue in the reactor was determined after each experiment and was typically a few percent, depending on the reaction conditions.

A typical experiment was performed using the following steps. The reactor was loaded with biomass and was mounted between the boiler tube and the expansion vessel. The reactor and expansion vessel were flushed with $N_2$ gas and pressurized to about 15 bar. After the boiler tube had been loaded with water, typically 275 ml, the tube furnace was turned on. Pre-heating of the reactor region was commenced 20-30 minutes before reaching the set-point value of the boiler. Reaching the set-point value triggers the computer controlled pulse sequence, i.e. the repeated sequence of dissolving the biomass. This comprises the steps of opening and closing valves in a predefined sequence and with predefined delay times. The total time for dissolution of the biomass depended primarily on the number of pulses and the reaction time, and was typically 1-4 minutes. The filling time and flushing times used for most sequences were 200 ms and 1500 ms respectively, while the reaction time was varied in the interval 1-15 s for optimization purposes. For safety reasons the system was cooled down using fans before the reactor was detached from the system and also before the boiler was refilled with water for the next experiment. The pressure in the boiler started at about 350 bar and dropped step by step to about 150 bar as it is emptied of water. The pressure in the reactor peaked during each fill and subsequently decayed before it finally dropped to the pressure of the expansion vessel when the bottom valve was opened. The boiler temperature was in principle constant during the pulse sequence, whereas the temperature before and after the reactor peaked during each pulse. The temperature profile increased initially after each pulse because the water dissipated heat to the surrounding tubing and reactor. At the end of the sequence there was a drop in temperature which was probably related to the decrease in boiler pressure.

When measuring the yield of monosaccharides from the performed experiments, it has been shown that at least a 20% yield is possible to achieve. Fact is that some of the performed experiments gave a glucose yield of about 20% and a total monomer yield of above 30%, in some cases about a total yield of 35%.

Below follows a more detailed description of some performed experiments.

Liquefaction Experiment No. 20100624-P01, Batch Set-Up 3010 mg of 31 thin pine sticks, about 10 cm long were loaded in the reactor. The boiler tube was filled with 275 g of deionized water. The reactor and expansion vessel were flushed with $N_2$ gas for a few seconds, and then pressurized to 15 bar. The tube furnace was turned on in order to heat the loaded water, and after 43 minutes the preheating of the reactor region was initiated. After additional 24 minutes the set-point value of 395° C. for the boiler water temperature was reached and the pulse sequence started. The pulse sequence parameters were: filling time=200 ms, reaction time=10 s, flush time=1500 ms, number of repetitions=20. At the onset of the pulse sequence the pressure inside the boiler was 335 bar. The amount of solution collected in the expansion vessel was 199 g. The residual biomass in the reactor was dried in an oven at 50° C., and was determined to be 116 mg. A small sample of the solution was filtered using a 0.45 μm syringe filter resulting in a clear slightly yellowish solution. The pH of the solution was 3.8.

As may be noted from the above, both the temperature and the reaction time are important parameters for controlling the liquefaction process according to the present invention. Moreover, from above it is evident that the process according to the present invention renders high yields although being a resource effective and environmental friendly process which is not dependent on any additives except the biomass feedstock and HCW.

As seen in FIG. 1, there is shown the different temperatures vs. time and hence the pulse temperature profile for a batch process experiment (namely 20100610) performed according to the same procedure as disclosed above. The different temperatures shown are T901, which is the temperature before the reactor, T903, the temperature after the reactor, T905, the temperature in the expansion vessel were the dissolved biomass, that is the product, is collected, and T705, which is the temperature in the boiler. From FIG. 1 it may be noted the temperature pulse appearance of the process and the short reaction times of from 1.5 up to 30 s, in this case only up to 15 s maximum as the temperatures are held comparatively high at the peaks, such as well above 300° C. during several of the pulses. It should also be noted that the boiler temperature set-point value of 395° C. is clearly shown, and this temperature should not be confused with the temperature inside the reactor, which is shown when viewing the differences in relation to the temperatures measured before and after the reactor. The temperature in the reactor may be seen as the average in between the temperatures measured before and after the reactor. The difference between the temperature in the boiler and this average temperature in the reactor is related to energy loses which always may exist in some amount.

Experiments for Flow Operations

Example 1. Break-Down of Microcrystalline Cellulose in a Single Reactor (Experiment No. V2110824)

A slurry consisting of 10% microcrystalline cellulose (Fluka) and millipore filtered water was prepared. The slurry was pumped using a membrane pump resulting in a flow of approximately 11 kg/hour through the system. Process temperatures in the range 283-324° C. were investigated and the pressure was around 230 bar. The residence time in the reactor zone depended slightly on the temperature, due to the temperature dependence of the fluid density, and was in the range of 3-3.7 seconds.

In table 1 below, the process parameters together with some of the decomposition products are shown. The oligomers as presented in the table are the sum of cellobiose, cellotriose, and cellotetraose, and longer oligomers are thus not included. The monomers in the table are predominantly glucose, but small amounts of anhydroglucose are also included. In FIG. 2 in the drawings, the compounds produced at the various temperatures are displayed, but in the plot anhydroglucose is added to the by-products. The amount of undesired breakdown products escalates at higher temperatures as can be seen in table 1. In order to obtain high yields of mono- and oligomers, also with a minimum of breakdown products, it is advantageous to use an iterative or serial process at a lower temperature, e.g. 310° C., where solubilized material is removed from the reactor and non-solubilized material is reprocessed.

TABLE 1

| Sample # | Temperature (° C.) | Residence time (s) | Oligomers (mg/ml) | Monomers (mg/ml) | Organic acids (mg/ml) |
| --- | --- | --- | --- | --- | --- |
| V2110824-1 | 283 | 3.7 | 1.5 | 1.7 | 0.3 |
| V2110824-2 | 295 | 3.4 | 5.7 | 3.8 | 0.6 |
| V2110824-3 | 310 | 3.3 | 24.9 | 22.8 | 2.2 |
| V2110824-4 | 324 | 3.0 | 3.4 | 50.8 | 21.5 |

As may be noted in FIG. 2, relating to the table 1 above, there is shown the decomposition of cellulose, in a 10% slurry, as a function of temperature when the residence time was about 3.4 seconds.

Example 2. Break-Down of Microcrystalline Cellulose in a Single Reactor (Experiment No. V2110907)

A slurry consisting of 10% microcrystalline cellulose (Fluka) and millipore filtered water was prepared. The slurry was pumped using a membrane pump resulting in a flow of approximately 21 kg/hour through the system. Process temperatures in the range 301-350° C. were investigated and the pressure was around 220 bar. The residence time in the reactor zone depended slightly on the temperature, due to the temperature dependence of the fluid density, and was in the range of 1.5-1.7 seconds.

In table 2 below the process parameters together with some of the decomposition products are shown. The oligomers as presented in the table are the sum of cellobiose, cellotriose, and cellotetraose, and longer oligomers are thus not included. The monomers in the table are predominantly glucose, but anhydroglucose and erythrose are also included, in significant amounts at the highest temperatures. In FIG. 3 the compounds produced at the various temperatures are displayed, but in the plot anhydroglucose and erythrose is added to the by-products, and only glucose and fructose are shown as monomers. Comparing with example 1 we see that a shorter reaction time requires higher temperatures for similar break-down of cellulose. There is however not just a shift in temperature, but also it can be seen that the combination of short reaction time and high temperature increases the total monomer and oligomer yield.

TABLE 2

| Sample # | Temperature (° C.) | Residence time (s) | Oligomers (mg/ml) | Monomers (mg/ml) | Organic acids (mg/ml) |
|---|---|---|---|---|---|
| V21100907-1 | 301 | 1.7 | 3.6 | 2.6 | 0.2 |
| V21100907-2 | 311 | 1.7 | 8.5 | 3.3 | 0.6 |
| V2110907-3 | 321 | 1.6 | 22.1 | 9.3 | 1.5 |
| V2110907-4 | 329 | 1.6 | 33.7 | 29.8 | 2.9 |
| V2110907-7 | 340 | 1.5 | 11.2 | 64.2 | 7.1 |
| V2110907-8 | 350 | 1.5 | 4.0 | 70.8 | 13.4 |

As may be noted in FIG. 3, relating to the table 2 above, there is shown the decomposition of cellulose, in a 10% slurry, as a function of temperature when the residence time was about 1.6 seconds.

The invention claimed is:

1. Process for a controlled conversion of a biomass feedstock, wherein the process comprises:
    loading the biomass feedstock to at least one reactor;
    liquefaction of the biomass feedstock into a monomer and/or oligomer sugar mixture in said reactor by treatment in hot compressed liquid water at sub- and/or super-critical condition; and
    removal of the monomer and/or oligomer sugar mixture to avoid continued detrimental decomposition;
    wherein the liquefaction is performed at a temperature of at least 280° C. during a reaction time t of from 1.5 to 30 s; and wherein the liquefaction is performed in one cycle or by repeated cycles by injection of hot compressed water; and further
    wherein each injection of hot compressed water applies a temperature pulse at a sub- or super-critical condition in the reactor to allow for liquefaction of the biomass feedstock, said pulse involving applying a pulse start temperature during a temperature increase time and allowing for liquefaction reaction to occur during the reaction time t.

2. Process according to claim 1, wherein the liquefaction is performed at a temperature of below 374° C.

3. Process according to claim 1, wherein the liquefaction is performed at a temperature in the range of 280-350° C.

4. Process according to claim 1, wherein the liquefaction is performed at a temperature in the range of 300-350° C.

5. Process according to claim 1, wherein
    loading of the biomass feedstock is performed by preloading biomass into a batch reactor;
    liquefaction is performed in one cycle or repeated cycles by injection of hot compressed water to the batch reactor; and
    solubilized material is discharged from the batch reactor after the reaction time t for each cycle.

6. Process according to claim 1, wherein
    loading of the biomass feedstock is performed by cyclic loading of biomass into a single batch reactor or into a series of batch reactors so that said reactor(s) is refilled after complete biomass liquefaction;
    liquefaction is performed in one cycle or by repeated cycles by injection of hot compressed water to the batch reactor or series of batch reactors; and
    solubilized material is discharged from the batch reactor after the reaction time t for each cycle.

7. Process according to claim 1, wherein
    loading of the biomass feedstock is performed by cyclic loading of biomass into at least one flow reactor;
    liquefaction is performed by injection of hot compressed water to said flow reactor by one cycle; and
    solubilized material is flowed downstreams from the flow reactor to a non-reactive zone.

8. Process according to claim 1, wherein separation of a lignin component is performed by removal of non-solubilized material from at least one reactor.

9. Process according to claim 1, wherein
    loading of the biomass feedstock is performed by continuous loading of biomass into at least one flow reactor;
    liquefaction is performed by continuously injecting hot compressed water to said flow reactor; and
    solubilized material is flowed downstreams from the flow reactor to a non-reactive zone.

10. Process according to claim 7, wherein several flow reactors are used and wherein at least one flow reactor is a loading reactor and at least one flow reactor is a reaction reactor.

11. Process according to claim 1, wherein
    the biomass feedstock is a slurry which is continuously loaded to a flow reactor;
    said slurry is rapidly warmed to sub- or super-critical condition; and
    solubilized material is flowed downstreams from the flow reactor to a non-reactive zone.

12. Process according to claim 1, wherein the process further comprises
    removal of non-solubilized material;
    wherein lignin is separated at the step of removal of non-solubilized material, and
    wherein the removed non-solubilized material is reprocessed.

13. Process according to claim 1, wherein the process is performed free from any chemicals besides hot compressed water and the biomass feedstock.

14. Process according to claim 1, wherein at least one pH lowering additive is added to the process.

15. Process according to claim 1, wherein the pulse start temperature is at least 280° C.

16. Process according to claim 1, wherein the pulse start temperature is in the range of 300° C.-350° C. and the reaction time t is 1.5 to 15 s.

17. Process according to claim 1, wherein the process further comprises a subsequent step of hydrolysis, fermentation, or a combination thereof.

18. Process according to claim 1, wherein the biomass feedstock is a lignocellulosic biomass feedstock.

19. Process according to claim 9, wherein several flow reactors are used and wherein at least one flow reactor is a loading reactor and at least one flow reactor is a reaction reactor.

20. Process according to claim 1, wherein the liquefaction is performed at a pressure held at a level high enough so that the hot compressed water is in liquid form.

* * * * *